(12) United States Patent
Seul

(10) Patent No.: US 9,082,145 B2
(45) Date of Patent: Jul. 14, 2015

(54) WEB-HOSTED ENGINE FOR CONTINUOUSLY IMPROVING THE IDENTIFICATION OF SAFER PRODUCTS FOR ADMINISTRATION

(71) Applicant: Michael Seul, Basking Ridge, NJ (US)

(72) Inventor: Michael Seul, Basking Ridge, NJ (US)

(73) Assignee: BioInventors & Entrepreneurs Network LLC, Warren, NJ (US)

( * ) Notice: Subject to any disclaimer, the term of this patent is extended or adjusted under 35 U.S.C. 154(b) by 11 days.

(21) Appl. No.: 14/309,850

(22) Filed: Jun. 19, 2014

(65) Prior Publication Data

US 2015/0032632 A1   Jan. 29, 2015

Related U.S. Application Data

(63) Continuation-in-part of application No. 13/190,163, filed on Jul. 25, 2011, now Pat. No. 8,932,989.

(60) Provisional application No. 61/990,906, filed on May 9, 2014.

(51) Int. Cl.

| | | |
|---|---|---|
| *G01N 33/46* | (2006.01) | |
| *G06Q 30/06* | (2012.01) | |
| *G06F 19/00* | (2011.01) | |
| *G06Q 30/00* | (2012.01) | |
| *C40B 20/04* | (2006.01) | |
| *C40B 50/10* | (2006.01) | |
| *C40B 50/16* | (2006.01) | |
| *G06G 7/48* | (2006.01) | |

(52) U.S. Cl.
CPC ............ *G06Q 30/0631* (2013.01); *C40B 20/04* (2013.01); *C40B 50/10* (2013.01); *C40B 50/16* (2013.01); *G06F 19/322* (2013.01); *G06F 19/3431* (2013.01); *G06F 19/3456* (2013.01); *G06Q 30/018* (2013.01); *B01J 2219/00576* (2013.01); *B01J 2219/00592* (2013.01); *B01J 2219/00722* (2013.01); *B01J 2219/00725* (2013.01); *G06F 19/34* (2013.01); *G06Q 2220/10* (2013.01)

(58) Field of Classification Search
CPC ............................. G06F 19/34; G06F 19/345
See application file for complete search history.

(56) References Cited

U.S. PATENT DOCUMENTS

| 7,957,983 B2 * | 6/2011 | Hoffman et al. ................... 705/2 |
| 8,135,595 B2 | 3/2012 | Dalton |
| 2010/0219241 A1 * | 9/2010 | Corwin et al. ................ 235/375 |
| 2012/0265446 A1 | 10/2012 | Janevski et al. |
| 2013/0252831 A1 | 9/2013 | Chen |

* cited by examiner

*Primary Examiner* — Eric S Dejong
(74) *Attorney, Agent, or Firm* — Eric P. Mirabel

(57) ABSTRACT

Genetic information relating to clinically significant attributes are generated as unique molecular signatures, which are provided to a subscriber to be carried as a card or in another form, including for display by a subscriber's computer or smart-phone or PDA. The signature is periodically updated as new clinically significant attributes become known. The process of updating the signature and using it to obtain suitable products (which don't have an unacceptable risk of generating an adverse reaction or outcome) is also described.

20 Claims, No Drawings

WEB-HOSTED ENGINE FOR CONTINUOUSLY IMPROVING THE IDENTIFICATION OF SAFER PRODUCTS FOR ADMINISTRATION

RELATED APPLICATIONS

This application claims the benefit of Provisional Application No. 61/990,906, filed May 9, 2014.

BACKGROUND

In the United States today, transfusion of incompatible blood is a significant factor contributing to morbidity and mortality especially for individuals whose clinical condition or disease—such as sickle cell disease, thalassemia and hematologic malignancies including leukemia and myelodysplastic syndrome—requires periodic transfusion of one or multiple types of blood cells. At present, a minimal degree of compatibility between donor and recipient "blood types" is ascertained in accordance with a "type & screen" paradigm by determining the major phenotypes, defined in terms of the antigens AB (which define the ABO blood groups) and RhD, and screening recipients for alloantibodies against other antigens, and only if such antibodies are detected identifying the antibody, or antibodies, in order to select donor cells lacking the corresponding antigen(s) ("antigen-negative blood") (Hillyer, C. D. et al., Blood Banking and Transfusion Medicine: Basic Principles & Practice, Elsevier Science Health Science 2002). The repertoire of serologic testing methodologies for addressing this task include: direct agglutination, immediate spin test, as well as indirect antiglobulin test (referred to as "TAT"; see I. Dunsford et al., Techniques in Blood Grouping, 2nd ed. Oliver and Boyd, Edinburgh (1967)). The TAT detects antibodies in the recipient's plasma that recognize one of the major antigens (A, B and RhD) expressed on a donor's erythrocytes which thereby can elicit an adverse transfusion reaction.

Reactions may vary in severity ranging from "none" to "severe" (Hillyer, C. D. et al., supra at p. 17). For instance, critical antigens in the ABO or Rh blood groups, if mismatched, can induce a severe adverse reaction, whereas antigen N, if mismatched, does not. The degree of severity also varies depending upon whether the subject is an adult or a newborn child. For example, an offending antigen S may cause only a mild adverse reaction in an adult but can cause severe hemolytic disease of the newborn. A primary clinical concern arises from the fact that transfusion reactions may entail the accelerated destruction of administered cells, thereby diminishing the efficacy of the therapeutic intervention. Thus, hematology patients undergoing chemotherapy often develop pancytopenias that, while initially caused by impaired hematopoieisis, often are exacerbated by antibody-mediated destruction of incompatible cells given during treatment; a case in point is thrombocytopenia: as patients become increasingly less responsive and not infrequently completely unresponsive ("refractory") to platelet transfusion, they are exposed to an increased risk of bleeding which may be fatal. To mitigate this risk, these patients receive more frequent transfusions to maintain at least a minimal platelet count, resulting in excess consumption of product; these patient also often require extended care in hospital, at significant excess expense (Meehan et al 2000, "Platelet Refractoriness: Utilization and Associated Costs in a Tertiary Care Hospital", American J of Hematology, 64: 251-256 (2000)).

Reducing the risk of allo-immunization, by preventing the exposure of the patient to unacceptably immunogenic epitopes, thus remains an important clinical concern, especially in the context of the emphasis on patient-centric and preventive medicine codified in the Affordable Care Act, Health and Human services website, at healthcare/rights/law/index.html).

The current practice of confirming the compatibility of units intended for transfusion for only the major antigens and, in the event, for additional antigens if corresponding specific antibodies are detected, is ill suited to advance this objective. In fact, this "re-active" approach often exacerbates the problem when patients require multiple transfusions. This is so because "antigen-negative" units invariably expose these patients to new allo-antigens and trigger the proliferation of antibodies whose identification in turn requires increasingly complex laboratory procedures followed by the search, often under time pressure, for increasingly less common donor units that lack all the cognate antigens for the antibodies now in the mix: a sisyphean task, with undesirable consequences for patients, who are needlessly exposed to increased clinical risk, and for payers, who bear the excess cost.

The re-active approach, in part, reflects the limitations of the available repertoire of serologic methods which are effective only when antibodies are already manifest. In addition, the extension of routine serologic typing to all clinically relevant antigens is precluded by the lack of appropriate reagents including antisera and the complexity and limited reliability of labor-intensive protocols requiring special expertise and training in immunohematology, particularly when encountering multiple alloantibodies or weakly expressed antigens. Sensitivity is another concern regarding the accuracy of the results, serotyping is based on the interpretation of agglutination patterns that reflect the level of antigen expression, and weakly expressed antigens may be missed.

In contrast, modern methods of DNA analysis such as those described in "BeadChip Molecular Immunohematology" (see Amazon's website under "BeadChip-Molecular-Immunohematology-Profiling-Analysis/dp/144197511X") are free from these limitations. Thus, the analysis of blood group genes at the DNA level provides a detailed picture of the allelic diversity that underlies phenotypic variability. As described in a number of sources (including, Hashmi et al., Transfusion, 45, 680-688 (2005)) available methodologies permit the simultaneous analysis of clinically significant single nucleotide polymorphisms within the genes encoding antigens in the Kell, Duffy, Kidd, MNS and other systems including the highly variable RhD and RhCE genes, Human Leukocyte Antigens, Human Platelet Antigens and others. See U.S. Pat. No. 7,612,193 (incorporated by reference). Furthermore, these methods can eliminate the need for costly reagents and complex and labor-intensive protocols for serologic analysis, as well as the need for repeat testing of recipients for antibodies to particular donor antigens, and help in addressing clinical problems that cannot be addressed by serologic techniques, such as: the determination of antigens for which the available antibodies are only weakly reactive; the analysis of recently transfused patients; or the identification of fetuses at risk for hemolytic disease of the newborn.

The benefit of identifying immunogenic epitopes on the basis of genotypes relating to the expression of transfusion antigens is to minimize or eliminate not only the risk of antibody proliferation with its adverse effects, but also the risk of immunizing recipients in the first place, and to enable the rapid selection of blood products for transfusion from a group of donors.

Thus, to reduce the risk of allo-immunization, and the antibody-mediated accelerated destruction of administered cells, it will be preferable to pro-actively align molecular signatures of recipient and candidate donor(s) by deploying modern methods of DNA analysis.

While DNA analysis is the de facto standard for identifying stem cell and solid organ donors, the prediction of (T-cell receptor) epitope configurations as a function of differences in DNA sequence between donor and recipient has remained a challenging and elusive task in that setting. Currently, tissue banks seek graft donors whose Human Leukocyte Antigen ("HLA") alleles must match the recipient's at multiple class I and class II loci to within not more than two mismatched positions to be acceptable. Thus, donors are assessed on the basis of sequence similarity, such that, when a perfect match is not available, graft selection is guided by mere rules of thumb that may deprive certain recipients of perfectly acceptable (stem cell as well as solid organ) transplants. A rational basis for assessing the impact of mismatched alleles on epitope configurations and the associated risk of an adverse reaction (such as graft rejection or graft-vs-host disease) remains to be established. (S. Feng, *Characteristics associated with Liver Graft Failure: The Concept of a Donor Risk Index," Am. J. of Transplantation*, Vol. 6, pp. 783-790 (2006); K. Lentine, "*Cardiovascular Risk Assessment Among Potential Kidney Transplant Candidates: Approaches and Controversies" Am. J. of Kidney Diseases*, Vol. 55, pp. 152-167 (2010).). In contrast, the use of DNA analysis, in the process described herein, forms a critical input to the exclusion of donor units that would expose the intended recipient to unacceptably immunogenic epitopes. Thus, the process described here differs from the genetic cross-matching currently used by tissue banks for the selection of stem cells for allogeneic transplants.

A problem in using DNA analysis for establishing molecular signatures is how to store genetic information in such a way as to permit the selection of suitable products for patients, especially when patients do not receive all treatment at the same institution: this often is the case with sickle cell patients in crisis, or hematology patients commencing treatment in the community setting who ultimately require tertiary care at another institution. The genetic information is more complex than is information obtained by serotyping, and the capability of interpreting it providing it in clinically actionable form is less widely available. An additional problem with genetic analysis is that, as new markers become known, their clinical significance must be assessed so that new markers, if significant, can be added to the analysis guiding the identification of compatible products for a patient. Accordingly, a system of storing and keeping current such information, and for allowing secure access to it for providing compatible products to a patient is needed.

Thus, to enable a pro-active approach to the selection of appropriate cells for transfusion, a viable process is needed by which to generate, make available to the patient in "portable" and preferably in "wearable" form, and maintain up-to-date the relevant clinical information provided by these methods while maintaining the confidentiality of the patient's personal information.

SUMMARY

Making personal genetic information and molecular attributes into a form which is attractive is one way to encourage individuals, potential future patients all, to carry such information with them, so that it is available when needed, even if the individual is unconscious or incoherent. Encrypting such information relating to clinically significant attributes and rendering it as a unique molecular signature allows making it more attractive and ensures that the information will remain confidential (even if observed by someone). By way of a system comprising a web-hosted service, the signature can then be provided to a individual subscribing to the service to be carried as a card or in another form, or to be displayed by an individual's computer or smart-phone or PDA. The signature can also be incorporated into jewelry, or tattooed on the skin, or be a computer readable chip, or be in any other form readily carried by the subscriber.

The system would also include a subscriber identification and authentication process, so that such health-related information can only be released by the subscriber to authorized persons. With such a system in place, for a subscriber in need of a cellular product (including blood or blood products), a secure order for such products would be placed such that suitable products are certified to lack clinically significant markers other than those the subscriber already expresses (as shown by decrypting the subscriber's molecular signature), or for products otherwise having a reduced risk of generating an adverse reaction.

The epitope profile must be anticipated to evolve as new clinically significant markers are identified, or the relative degree of significance of any known marker changes. Thus, a subscriber's molecular signature is never complete, and in fact, must be periodically updated, when new clinically significant markers are identified: a new molecular signature must then be generated and provided to the subscriber. Changes in degree of significance of markers can be dealt with by the website-holding entity matching the product and subscriber, by adjusting weighting, as described below.

In a format of deployment comprising a website accessible by a subscriber, the entire process, including the updating functions, can be performed as follows: identifying several of the subscriber's clinically significant molecular attributes which are known to be associated with adverse reactions or adverse clinical outcomes as a first unique subscriber molecular signature; encrypting this molecular signature and providing a first encrypted molecular signature to the subscriber. The unique molecular signature can function as a subscriber-identifying icon (recognized by the website) or optionally, another subscriber identifier for the website (e.g., a user name ID and password or another code) can be provided to the subscriber.

As new clinically significant attributes or markers are identified, the molecular signature provided to the subscriber is updated by being recalled, destroyed or superseded by a revised molecular signature, where the revised encrypted molecular signature includes encryption of all the subscriber's clinically significant molecular attributes. The revised encrypted molecular signature is provided to the subscriber and also preferably stored at the website. This updating process is repeated as other additional clinically significant markers are identified.

The molecular signature is used in selecting cellular products suitable for the subscriber because they reduce or eliminate the risk of alloimmunization and adverse clinical reactions. Suitable cellular products contain no significant antigens/epitopes other than those also expressed on the subscriber's own cells (such products designated as having a null allo-epitope profile), or, products which do not have a null allo-epitope profile but are nevertheless considered acceptable because the risk of a severe clinical reaction is below a threshold or the likelihood of an adverse clinical outcome is below a threshold. Optionally, the epitope profile of the product also can be reduced to a (donor) molecular signature.

In operation, after the subscriber is identified and a molecular signature is provided, the website receives a request for suitable products and the subscriber identifier (and preferably also the subscriber encrypted molecular signature, though that also may be stored already, at the website or elsewhere). The subscriber is authenticated by the signature or by the identifier, and then a request for suitable products is processed by the website. Once a suitable product is found, the website either allows the subscriber or its designee to directly transact business with the party holding the product, or stands between both parties and conducts a transaction with each in order to fill the order (see U.S. Pat. No. 8,504,388, incorporated by reference). The subscriber can be charged at any stage in the transaction or at multiple stages. The product request can be by a hospital, physician or other care provider, or by a supplier of blood products including a manufacturer, or by an intermediary such as a blood broker.

DETAILED DESCRIPTION

Definitions

Genotype: a string comprising pairs of (possibly identical) letters from the set {A,C,T,G}, over a selected set of variable sites (eg "SNPs"): AT,TT,GC,CA, . . . . The invention includes reducing portions of the genotype to a molecular signature, which is provided to the subscriber.

Allele, Haplotype: a string, or set of strings, comprising letters from the set {A,C,T,G} over a selected set of variable sites; a genotype represents the superposition of two alleles or haplotypes Allo-epitope profile: set of known epitopes of interest NOT expressed by the subscriber.

Alleles and haplotypes (but NOT the genotype) encode epitope(s) associated with antigens of interest: in order to determine a subscriber's allo-epitope profile, alleles or haplotypes must be recovered from the genotype and must be mapped to variable positions in the amino acid sequence for antigens of interest: for present purposes, epitopes may be identified as a minimal set of one or more variable amino acid positions that uniquely identify an allele at a specific locus (e.g. HLA-A,-B,-C);

Cellular Products: products containing cells, including blood, blood products, red blood cells, platelets, granulocytes, leukocytes and stem cells, and including markers relating to blood type and tissue type as well as tissues and organs.

Clinical Allo-Immunization Risk profile: an attribute of an individual with a specific epitope profile, related to the probability that this individual, in the course of receiving N cellular products chosen at random from a typical donor population, will be exposed to one or more of the epitopes s/he lacks (=allo-epitopes) and, given corresponding SCAIR factors, will form antibody against at least one of these allo-epitopes.

Encrypted Molecular Signature: an encrypted representation of the Molecular Signature from which it is derivable by decryption; a genotype, as defined, may serve as an encrypted Molecular Signature; such an encrypted Molecular Signature preferably is provided in a wearable format, as disclosed herein.

Molecular Signature, aka Molecular Attribute Profile: minimally, one of:
    allo-epitope profile of subscriber (this can be released to an authorized and properly authenticated subscriber representative such as a care provider); or
    epitope profile of a cellular product, preferably derived from the underlying alleles or haplotypes recovered from the genotype.

the molecular signature comprising an epitope profile may be augmented by additional molecular attributes relating to the process of antibody formation, for example the subscriber's HLA alleles governing peptide presentation to T-cells in the process of antibody synthesis.

Score for Clinical Allo-Immunization Risk ("SCAIR"); aka SCAIR factor: a property of an epitope expressing its immunogenicity, namely, the (conditional) probability that an individual who lacks this epitope, when exposed to it, forms an antibody; this Score may be derived from clinical immunization records and updated if such probability increases.

In operation, a molecular signature is generated for a system subscriber, and provided to the subscriber, in encrypted form so as to preserve the confidentiality of the individual's molecular signature even when this is publicly displayed, or, upon authentication, in decrypted form to the subscriber or to someone designated by the subscriber (e.g., a health care provider, a hospital, or the suppliers of blood products including manufacturers, or intermediaries such as blood brokers). The subscriber's allo-epitope profile, derivable from the signature,—incorporates only the clinically significant epitopes known at the time of generating the signature. However, new clinically significant epitopes may be periodically identified as larger groups of individuals are characterized by the more widespread application of methods of DNA analysis including new methods of DNA sequencing. The system may require a degree of acquiescence by the relevant community before a new epitope is added to the existing signature, including but not limited to publication in a peer-reviewed journal, a statistically significant increase in reactions where the epitope is in cellular products provided to all-epitope negative subscribers, or acceptance of the epitope as significant by clinicians. In order to ensure the molecular signature carried by the subscriber accounts for all significant epitopes, new and other, the molecular signature must be periodically updated.

The encrypted molecular signature can be in a wearable form (as part of a wristband, necklace, ankle bracelet, or tattoo), can be a card carried by the subscriber, or can be an electronic display—to be displayed by a subscriber's computer or smart-phone or PDA. It is preferable if it can be scanned, so that it can be readily authenticated by the website. Additional authentication icons may also be provided to the subscriber. These are also preferably scannable. Such icons may include, but are not limited to, gravatars, as described in U.S. Pat. No. 7,747,602 (incorporated by reference).

In order to update the molecular signature, the existing signature must be recalled or destroyed when the new updated one is issued. Accordingly, carrying the signatures in a readily disposable form, such as a card or electronic display, is preferred for the subscribers.

Cellular products, preferably, immediately upon being collected at a donor institution, preferably prior to stocking and distributing them, also can be classified by molecular signature, so that, by comparing the molecular signature of a subscriber to that of prospective donor cells, cells unsuitable for that specific recipient are readily identified and excluded. If the products are obtained from a person who already has an assigned molecular signature, the products would simply be marked with the same signature. Otherwise, it would be necessary to determine the significant epitopes carried by the products, either serologically or by way of genotyping.

The molecular signature is also useful in determining suitability of certain drugs for administration. For example, the dosage of warfarin can be optimized by evaluating a set of mutations related to certain enzymes such as cytochrome P450. These mutations or similar ones related to other drugs could also be included in a molecular signature.

In operation, generating and providing a subscriber a molecular signature by way of a website would include the specific steps of (wherein the website could levy a charge for each step or step combination):

generate an identifier for a subscriber;
provide a program to generate "MyImmunoMolecularSignature" performing these steps:
generate genotype and render it in a representation that may include additional encryption, including: random sequence of position indices; optionally, add "noise", e.g. shape, color, orientation, or boundaries; render pattern & combine with a code, eg QR code (U.S. Pat. No. 5,726,435, incorporated by reference) or other one or two dimensional array or bar code; the code may include versioning information
store encryption key on server associated with subscriber identifier (and/or subscriber molecular signature)
notify subscriber: offer choice of medium on which to render encrypted molecular signature, such as card, display etc.

The steps of providing to the subscriber or its designee the relevant epitope information, on request, would be as follows:
generate genotype and derive associated molecular signature, using additional ("private") information and/or the Clinical AlloImmunization Risk profile:
subscriber or designee logs in, eg, using scanned QR code associated with signature
authenticate subscriber, eg, by matching subscriber identifier, password
validate molecular signature via stored decryption key
record request, requester ID (e.g. care provider)
reconstruct ("decrypt") epitope profile, from encrypted molecular signature uploaded by subscriber; identify risk profile
optionally translate epitope profile into desired format e.g. Electronic Health Record: HL7, see International Organization for Standardization website
transmit to authenticated subscriber
obtain electronic confirmation
record transaction The steps of identifying a suitable product would include most of the same steps as providing the subscriber epitope information (as above), plus the steps of providing the identity of suitable products to the subscriber or its designee. Alternatively, the product could be identified and purchased by the website operator, and then provided to the subscriber or its designee.

As noted, the subscriber may be administered products which contain significant epitopes the subscriber does not express, if a determination is made that the cumulative risk (over multiple transfusions) of an adverse reaction and/or adverse clinical outcome is not significant. The first step in arriving at the determination is therefore to determine the SCAIR factor—which indicates the risk that the subscriber will form antibodies to the foreign epitopes in the product. Even if the SCAIR factor is relatively high, that does not end the inquiry, as generation of antibodies alone does not necessarily mean there will be a significant adverse reaction Thus, added steps in determining suitable products include:
analyzing the similarities and differences between the subscriber's clinically significant genetic markers and the epitopes they encode, and the clinically significant genetic markers of candidate products and the epitopes they encode, namely by deriving and comparing molecular signatures, and applying weights to said similarities and differences to generate a clinical risk estimator which estimates the risk of significant adverse subscriber reactions or adverse clinical outcomes for each of said available products, where the weighting is such that the severity of the adverse subscriber reactions or adverse clinical outcomes is reflected by said risk estimator function;
identifying product(s) for administration for which the clinical risk estimator is below a cut-off level, and providing such products or their identities to the subscriber or its designee.

The weights accorded to different epitopes derived from the likelihood of antibody formation upon exposure, may be adjusted to take into account additional information as it becomes available from sources including the scientific literature, researchers, clinicians, published studies and other sources. Preferably, weights will be derived from SCAIR factors of known epitopes; however, once an antibody is formed, the appropriate SCAIR factor is updated to indicate the increased clinical risk incurred by exposing that subscriber to the cognate antigen (thereby encompassing current practice of selecting "antigen-negative" units): this is important especially for epitope's with a low original value of the SCAR factor.

The specific methods and processes described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process for improving the identification and administration of safer products, including cells and cell-derived products for administration to subscribers, such that the products identified entail a lower risk of adverse reactions or adverse outcomes when administered to a subscriber, wherein the process accommodates additional clinically significant attributes, once these are determined to be significant, comprising the following steps:
   a. storing a unique subscriber identifier in a device controlled by the subscriber;
   b. generating and updating an encrypted molecular signature for the subscriber by:
      b1. encrypting several of the subscriber's clinically significant molecular attributes which are known to be associated with adverse reactions or adverse clinical outcomes as a first encrypted subscriber molecular signature;
      b2. sending the first encrypted molecular signature to the device whereby the first encrypted molecular signature is stored in the device;
      b3. identifying additional clinically significant molecular attributes that are to be added to the first molecular signature;
      b4. encrypting all the subscriber's clinically significant molecular attributes as a new molecular signature and sending it to the device whereby storing the new molecular signature is stored in the device;
      b5. repeating steps b1 to b4 as other additional clinically significant attributes are identified;
   c. receiving or obtaining the profile of the clinically significant attributes of candidate products to be administered to the subscriber; and
   d. analyzing the similarities and differences between the subscriber's molecular signature and the profile of the products to be administered to said subscriber, and administering products which either:
   do not contain any clinically significant attributes which the subscriber does not also express; or
   contain some clinically significant attributes which the subscriber does not express but said some clinically significant attributes do not render the product unacceptably unsafe based on the anticipated severity of the adverse subscriber reaction or adverse clinical outcome; and
   e. receiving at a website a request from a patient or the patient's designee for products suitable for being administered to the patient, and the patient identifier and encrypted molecule signature; authenticating the patient identifier; decoding the signature to recover the molecular signature, and transmitting to the authenticated requestor the attributes of products suitable for being administered to the patient.

2. The process of claim 1 further including, in the case where the products possess some of the same clinically significant attributes as the new molecular signature, identifying those which are acceptably safe by applying weights to said similarities and differences to generate a clinical risk estimator which reflects the risk of adverse recipient reactions or adverse clinical outcomes for each of said products; and identifying the product(s) for administration which are associated with a weighted clinical risk for the recipient below a cut-off level.

3. The process of claim 1 further including identifying products which are acceptably safe based on the risk of antibody formation upon administration of a product, and identifying, by antigen or epitope profile, the product(s) to be excluded from administration which are associated with a risk of antibody formation above a cut-off level.

4. The process of claim 2 wherein the likelihood of destruction of administered cells also is reflected by said clinical risk estimator.

5. The process of claim 2 wherein the likely severity of the adverse subscriber reactions or of adverse clinical outcomes also is reflected by said clinical risk estimator.

6. The process of claim 3 wherein determining the risk of antibody formation includes determining SCAIR factors for the patient's allo-epitopes.

7. The process of claim 1 further including: receiving at the website a request from a patient or the patient's designee for products suitable for being administered to the patient, and the patient identifier and encrypted molecular signature; authenticating the patient identifier; decoding the signature, to recover the molecular signature including the corresponding allo-epitope or CAIR profile; and transmitting to the authenticated requester the attributes of products suitable for being administered to the patient.

8. The process of claim 1 wherein the encrypting further includes the following steps:
   encrypting a representation of the patient's molecular signature as a pattern of distinct shapes or colors; and
   transmitting said pattern to the patient.

9. The process of claim 8 wherein the pattern of distinct shapes or colors is rendered on a card, or is in wearable form for display on the subscriber's person, or in form for electronic display on a computer or smart-phone or PDA.

10. The process of claim 1 wherein all stored subscriber molecular signatures, patterns and other associated subscriber information and medical records are accessible at the web-site, but only to the subscriber and the subscriber's designee.

11. The process of claim 1 wherein the patient's clinically significant molecular attributes in a molecular signature associated with likely antibody formation include epitopes or antigens expressed on circulating blood cells, such as red blood cells, platelets, granulocytes, leukocytes and stem cells, including molecular attributes relating to blood type and tissue type.

12. The process of claim 1 wherein there are charges associated with accessing or using the web-site, as well as for identifying products suitable for administration.

13. The process of claim 8 wherein the pattern is worn as jewelry or displayed on a bracelet, or is tattooed on the skin, or is embedded in a computer readable chip carried by the subscriber.

14. The process of claim 8 wherein the pattern is a one or two dimensional array or bar code.

15. The process of claim 1 wherein the unique subscriber identifier and the subscriber's clinically significant molecular attributes are stored in a database associated with the website.

16. The process of claim 1 wherein the molecular attributes include genetic markers.

17. The process of claim 1 further including inactivating the first encrypted subscriber molecular signature.

18. The process of claim 1 wherein the encrypted molecular signature is generated by encrypting the subscriber's clinically significant molecular attributes, or the encrypted molecular signature is the subscriber's genotype and the device can electronically transmit the encrypted molecular signature.

19. The process of claim 1 wherein the unique subscriber identifier is the encrypted molecular signature.

20. A process for improving the identification and administration of safer products, including cells and cell-derived products for administration to subscribers, such that the products identified entail a lower risk of adverse reactions or adverse outcomes when administered to a subscriber, wherein the process accommodates additional clinically significant attributes, once these are determined to be significant, comprising the following steps:
  a. storing a unique subscriber identifier in a device controlled by the subscriber;
  b. generating and updating an encrypted molecular signature for the subscriber by:
    b1. amplifying using a polymerase chain reaction portions of a subscriber's genome incorporating the subscriber's clinically significant molecular attributes;
    b2. encrypting several of the subscriber's clinically significant molecular attributes which are known to be associated with adverse reactions or adverse clinical outcomes as a first encrypted subscriber molecular signature;
    b3. sending the first encrypted molecular signature to the device whereby the first encrypted molecular signature is stored in the device;
    b4. identifying additional clinically significant molecular attributes that are to be added to the first molecular signature;
    b5. encrypting all the subscriber's clinically significant molecular attributes as a new molecular signature and sending it to the device whereby the new molecular signature is stored in the device; and
    b6. repeating steps b2 to b4 as other additional clinically significant attributes are identified;
  c. receiving or obtaining the profile of the clinically significant attributes of candidate products to be administered to the subscriber; and
  d. analyzing the similarities and differences between the subscriber's molecular signature and the profile of the products to be administered to said subscriber, and administering products which either:
  do not contain any clinically significant attributes which the subscriber does not also express; or
  contain some clinically significant attributes which the subscriber does not express but said some clinically significant attributes do not render the product unacceptably unsafe based on the anticipated severity of the adverse subscriber reaction or adverse clinical outcome; and
  e. receiving at a website a request from a patient or the patient's designee for products suitable for being administered to the patient, and the patient identifier and encrypted molecule signature; authenticating the patient identifier; decoding the signature to recover the molecular signature, and transmitting to the authenticated requestor the attributes of products suitable for being administered to the patient.

* * * * *